United States Patent [19]
Khor et al.

[11] Patent Number: 5,882,850
[45] Date of Patent: Mar. 16, 1999

[54] METHOD FOR REDUCING CALCIFICATION OF BIOLOGICAL TISSUE USED IMPLANTABLE BIOPROSTHESES

[75] Inventors: Eugene Khor; Aileen Wee; Weng Keong Loke; Bee Li Tan, all of Singapore, Singapore

[73] Assignee: The National University of Singapore, Singapore

[21] Appl. No.: 949,617

[22] Filed: Oct. 14, 1997

Related U.S. Application Data

[63] Continuation of Ser. No. 633,559, Apr. 17, 1996, abandoned, and a continuation of Ser. No. 366,771, Dec. 30, 1994, abandoned.

[51] Int. Cl.⁶ ..................................................... A01N 1/02
[52] U.S. Cl. .................. 435/1; 8/94.11; 623/2; 623/11
[58] Field of Search ...................... 435/1, 240.2; 8/94.11; 623/2, 11, 901

[56] References Cited

U.S. PATENT DOCUMENTS

| | | | |
|---|---|---|---|
| 3,966,401 | 6/1976 | Hancock | 8/94.11 |
| 4,050,893 | 9/1977 | Hancock | 8/94.11 |
| 5,336,616 | 8/1994 | Livesey | 435/240.2 |
| 5,368,608 | 11/1994 | Levy | 8/94.11 |

*Primary Examiner*—Ralph Gitomer
*Attorney, Agent, or Firm*—Birch, Stewart, Kolasch & Birch, LLP

[57] ABSTRACT

Biological materials are treated with an organic chemical agent, dimethyl sulfoxide, to delay the onset of in vivo calcification. The biological materials so treated become resistant to calcification over a prolonged period with no known deleterious effects to the host. The procedure involves the incubation of the natural biological materials in the chemical agent, prior to or after glutaraldehyde fixation, at room temperature or at temperatures up to 60° C. Materials that can be treated with this process include biological materials intended for bioprostheses use, such as porcine aortic valves, porcine aortic valve leaflets, bovine, equine and porcine pericardium, aortic homografts, reconstituted collagen, and the like suitable for invasive, or in-dwelling use in a human or animal body.

12 Claims, No Drawings

METHOD FOR REDUCING CALCIFICATION OF BIOLOGICAL TISSUE USED IMPLANTABLE BIOPROSTHESES

This application is a continuation, of application Ser. No. 08/366,559 filed Apr. 17, 1996, now abandoned of application Ser. No. 08/366,771 filed on Dec. 30, 1994, now abandoned.

BACKGROUND OF THE INVENTION

1. Field of the Invention

The present invention relates generally to biological materials that are resistant to in vivo calcification. More particularly, the present invention relates to the treatment of biocompatible natural materials, such as porcine heart valves, bovine pericardium, porcine pericardium and equine pericardium with dimethyl sulfoxide as the anticalcification agent. In particular, the present invention relates to treatment of the above biocompatible materials which have been, or are to be, treated by fixation in a glutaraldehyde solution, with dimethyl sulfoxide as the anticalcification agent.

2. Description of the Related Art

Cardiac valve replacement remains the major alternative in the treatment of severely diseased heart valves. Valve replacements can be from various sources and of various designs, all intended to imitate the function of the natural human heart valve. Currently, the major types of valve replacements are mechanical heart valves, bioprosthetic heart valves, and aortic homografts.

The mechanical valves in use today are of various designs and materials. Their performance in vivo have been shown to be good and reliable. However, their attributes are often offset by complications that can arise with the use of this type of valve, mainly thrombosis, which, if untreated, can lead to valvular failure. The possibility of thrombosis often requires patients receiving this type of valve to receive anticoagulant treatment, a lifetime inconvenience. Furthermore, catastrophic failure, which is a situation where the material used to make the component that controls blood flow breaks, is an occasional high risk factor.

In contrast, bioprosthetic heart valves, typically fabricated from porcine aortic valves or bovine pericardium, have better hemodynamics than mechanical valves, in that they provide blood flow characteristics closely approximating physiological blood flow. Moreover, in most cases, bioprosthetic valves do not require patients to be on anticoagulation treatment because thrombosis is unlikely. However, prolonged residence in vivo has lead to calcification of the valve material, in particular where the bioprosthetic valve has been prepared by a process involving glutaraldehyde fixing. This calcification can lead to the clinical failure of bioprosthetic heart valves, at a failure rate that is higher for younger patients. Therefore, the use of bioprosthetic heart valves has been limited because of the susceptibility of the biomaterial to calcification. Similarly, human aortic homograft implants have also been observed to undergo calcification involving the valvular tissue as well as the adjacent aortic wall.

Nevertheless, the favorable features of the bioprosthetic heart valve make it a desirable candidate for continued use.

Bioprosthetic heart valves are typically fabricated by a process including fixation of the biocompatible material, usually bovine pericardium or porcine aortic valves, in glutaraldehyde solution, which functions as a tissue preservative. This glutaraldehyde solution has been indicated as a possible major contributor to biomaterial calcification. It is believed that glutaraldehyde is released from the biomaterial after implantation, which leads to a local cytotoxic environment. This cytotoxic environment leads to the presence of cellular debris, which may provide starting points for calcification.

However, attempts to replace the glutaraldehyde fixation process have been unsuccessful to date, and glutaraldehyde fixation remains the method of choice for preserving tissue and preparing it for implantation as a biomaterial.

Efforts to improve the long-term inhibition of calcification via incorporation of anticalcification agents have also been unsuccessful to date. For example, treatment with Fe(III) has been unsuccessful due to diffusion of the Fe(III) out of the treated tissue. Similar problems can be expected to be encountered with Al(III), as well as potential side effects, such as mental disorders, associated with aluminum.

As a result, there remains a need for a method of long-term calcification prevention suitable for use with glutaraldehyde fixed bioprosthetic heart valves and similar implant devices, such as arterial grafts and other tubular duct replacements prepared from arteries, veins, human umbilical cords, etc.

SUMMARY OF THE INVENTION

The present inventors have discovered that, surprisingly, dimethyl sulfoxide (hereafter known as "DMSO") can delay the onset of in vivo calcification of bioprosthetic materials. There are no known examples of the use of this particular agent to inhibit calcification of bioprosthetic materials. Furthermore, this agent is not known to be toxic to living tissue.

It is therefore an object of the present invention to provide a process for the production of biological materials having increased long-term resistance to in vivo calcification, for implantation in the human or animal body by treatment with DMSO.

More specifically, it is the object of the present invention to provide biological materials which will allow the widespread use of bioprosthetic heart valves with reduced risk of valvular failure, and increased implant lifespan.

It is a further object of the present invention to provide biological materials exhibiting anticalcification properties wherein said properties are imparted to the material at the time of manufacture, thereby avoiding treatment after implantation, and decreasing complications.

These and other objects and advantages of the present invention are obtained by providing a method for treating biological material, comprising contacting biological material with a solution comprising dimethyl sulfoxide in an amount and for a period of time sufficient to inhibit calcification of said biological material after implantation into a human or animal body. This contacting step may be combined with preserving of the biological material by contacting with a fixing agent, e.g., glutaraldehyde, prior to, or subsequent to, the dimethyl sulfoxide solution treatment, which may comprise immersing said biological material in a solution comprising dimethyl sulfoxide at a temperature of from about 18° C. to about 60° C., for a time period ranging from about three minutes to about 48 hours.

The dimethyl sulfoxide solution may be neat dimethyl sulfoxide, or may be adjusted to a physiological pH, e.g., a pH of 7.40, by buffering in accordance with methods known in the art. In addition, the dimethyl sulfoxide solution may be admixed with fixing agent, water, or physiological saline.

The biological material may be of animal origin, as discussed in more detail below, or a human homograft, or may be of synthetic origin, such as reconstituted collagen.

The objects and advantages of the present invention are also obtained by providing a biological material that has been treated according to the process discussed above.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The terms "biological material" and "biological tissue" as used herein refer to natural biocompatible materials suitable for implantation, usually derivable from various animal sources and parts of the anatomy. For example, the tissue may be derived from various animals, e.g., tissue of porcine, bovine, equine, yak, sheep, rabbit, or kangaroo origins. The tissue may be heart valves, pericardiums, dura mater, tendons, ligaments, aortic arch, or carotid artery. Also encompassed by the invention are tissue suitable for skin patches, cardiac patches, pericardial patches, aortic patches, and tympanic membranes.

As pointed out above, the biological material may be of synthetic origin, such as reconstituted collagen, or may be a human homograft or autologous tissues, such as tissue obtained from the patient's pericardium or fascia lata. Human homografts are usually cryopreserved, and should be treated according to the present invention after thawing, with or without fixation by glutaraldehyde or other fixing agent. The concentrations of DMSO used to treat the homograft or autologous tissues according to the present invention are much higher than those suitable for cryopreservation.

The exact mechanism of the inhibition of calcification of biological tissue by DMSO is as yet unknown. However DMSO, being an organic chemical reagent, may remove phospholipids or other deleterious materials, speculated to initiate calcification, present in natural tissue from the biological tissue. Second, DMSO may crosslink or promote crosslinks with the collagen matrix or further crosslinks of glutaraldehyde or other fixing agent within the tissue. Third, DMSO may also cap the free ends of glutaraldehyde or other fixing agent molecules, thereby reducing the deleterious effects attributed to these free ends.

The DMSO to be used should be of an acceptable grade, typically HPLC grade or equivalent and can be used neat, i.e., as obtained from the vendor, or in varying concentrations with water or non-toxic organic reagents from 1% to 100%. Suitable non-toxic organic reagents include isopropanol, ethanol, and glycerol. If necessary or desirable, the DMSO may be sterilized using art recognized techniques.

The DMSO used can also be adjusted to a physiological pH, e.g., 7.40, with various buffers, for example HEPES (N-2-hydroxyethylpiperazine-N'-2-ethanesulfonic acid). The buffers are preferably stable, non-interacting with the fixation process or with the DMSO treatment process (i.e., the buffers do not react with the fixing agent or prevent the fixing agent from achieving proper fixation of the tissue), and have a buffering capacity sufficient to maintain an acceptable pH. The choice of an appropriate buffer and its concentration depends upon the specific tissue preparation conditions. The buffer may be conventional phosphate-buffered saline, or may include borate, carbonate, bicarbonate, cacodylate, MOPS (2-(N-morpholino)propanesulfonic acid, PIPES (1,4-piperazinediethanesulfonic acid) or TRIS (tris(hydroxymethyl)aminomethane). Desirably the DMSO/buffer concentrations are 90% DMSO/10% HEPES buffered saline, or 100% DMSO, at 25° C. to 37° C., for prevention of calcification. However, any concentration of DMSO between 0.5% and 100% could be used.

The DMSO can also be used in combination with glutaraldehyde or other fixing agent, as well as with water, buffer etc. as stated above. The duration of immersion may be varied from a few minutes up to 48 hours, more particularly from 1 to 24 hours. Immersion of the biological material in DMSO can be conducted from slightly above 18° C., which is the melting point of the chemical agent, to approximately 60° C., more particularly 25° C. to 37° C. Temperatures higher than 60° C. may result in denaturation of the biological material. The DMSO can be applied to fresh tissue, which can then be subjected to fixation (e.g., with glutaraldehyde) with reduced calcification, or to previously fixed tissue.

Suitable fixing agents for possible inclusion with the DMSO solution, as mentioned above, and for fixation of the tissue subjected to the process of the present invention include acyl azide, carbodiimides, polyglycidal ethers, cyanimide, glycerol, formaldehyde, and glutaraldehyde. The process of the present invention can also be applied to tissue that has been preserved by the method disclosed in U.S. Pat. No. 5,147,514. In addition, tissue which has been, or will be, subjected to pre- or post-glutaraldehyde treatments are also suitable for use in the present invention (e.g., tissue treated with chondroitin sulfate, protamine, diphosphonates, glutamic acid, amino acids, α-aminooleic acid, trivalent metal ions, and tissue which has been subjected to lipid extraction.

Determination of the concentration of DMSO solution and the immersion time and temperature within the above ranges can be made by those with ordinary skill in the art by evaluating the thermal shrinkage temperature (e.g., determined by hydrothermal or differential scanning calorimetry methods), amino acid analyses results, and other analytical results common to chemistry, biochemistry, microbiology, and histology, and described, for example, in Moore et al., 28 J. Biomed. Matls. Res. 611–618 (1994).

More specifically, each tissue type has a particular shrinkage temperature. Upon treatment with glutaraldehyde, the shrinkage temperature (usually around 60° C. to 70° C.) usually increases by 20° C. to 30° C. This increase is attributed to glutaraldehyde providing additional crosslinks, delaying the denaturation process to a higher temperature. With post-glutaraldehyde fixation treatment with DMSO, an additional increase in shrinkage temperature of 1° C. to 5° C. may be observed.

While shrinkage temperature provides a macroscopic picture of changes occurring in the tissue, amino acid analysis provides a microscopic indication of the effects of tissue treatment. Usually, a tissue sample is reacted with an acid which breaks down the tissue into collagen, and finally, into its constituent amino acid residues. Typically, animal tissue has about 15 to 20 constituent amino acid residues. Analysis of the relative amounts of these amino acid residues can give quantitative information about the efficiency of crosslinking. For example, glutaraldehyde predominantly crosslinks tissue at the amino acid lysine. Amino acid analysis would show a significant reduction in the concentration of lysine of tissue fixed with glutaraldehyde, when compared to untreated tissue. This gives a quantitative value of the degree and efficiency of crosslinking by glutaraldehyde.

Preparation of natural-derived tissue for glutaraldehyde preservation may be done following methods known in the art, and described in, for example, U.S. Pat. Nos. 4,323,358, 3,966,401, and 4,050,893. Similar methods can be used to prepare the tissue for treatment according to the present invention when glutaraldehyde treatment is to occur after DMSO treatment.

Given below are several specific illustrative techniques and examples for producing calcification-resistant materials in accordance with the principles of the invention. Although directed primarily to the preparation of calcification-resistant heart valve components, the techniques described herein are applicable to the creation of any other device comprising biological materials of the type used in surgically implanted devices. It should be noted that the range of DMSO usage and immersion periods given in these illustrative techniques are for illustration purposes only, and can be varied to achieve an optimal balance of immersion time and maximal effectiveness. Moreover, these illustrative methods and examples are for purposes of illustrating the present invention, and are not to be construed as limiting of the claims.

ILLUSTRATIVE METHODS AND EXAMPLES FOR TREATING AND PREPARING BIOPROSTHETIC HEART VALVES

EXAMPLE 1

Fresh biological material was immersed in DMSO for 24 hours, at a temperature of 25° C. Following immersion, the biological material was washed thoroughly in sterile buffered saline and stabilized in a 0.45% solution of glutaraldehyde in 0.05M HEPES buffer. The glutaraldehyde-preserved biological material was then fabricated into bioprosthetic heart valves and stored in glutaraldehyde at 4° C. for prolonged periods of time.

EXAMPLE 2

Freshly harvested biological material was stabilized in a 0.45% glutaraldehyde solution in 0.05M HEPES buffer before being immersed in DMSO for 24 hours at 25° C. Following treatment, the biological material was washed in sterile buffered saline and fabricated into bioprosthetic heart valves. However, the biological tissue so treated may be retained in, or returned to, the buffered saline and stored for 48 hours or more before being used to fabricate bioprosthetic heart valves.

EXAMPLE 3

The procedure described in Example 1 is followed, except that the duration of immersion is 1 hour.

EXAMPLE 4

The procedure described in Example 2 is followed, except that the duration of immersion is 1 hour.

EXAMPLE 5

The procedure described in Example 1 is followed, except that the temperature of immersion is 37° C.

EXAMPLE 6

The procedure described in Example 2 is followed, except that the temperature of immersion is 37° C.

EXAMPLE 7

The procedure described in Example 1 is followed, except that the concentration of DMSO is 70% in 0.05M HEPES buffered water or saline.

EXAMPLE 8

The procedure described in Example 2 is followed, except that the concentration of DMSO is 70% in 0.05M HEPES buffered water or saline.

EXAMPLE 9

Freshly harvested biological material is stabilized in 0.45% glutaraldehyde solution in 0.05M HEPES buffer after which the biological material is immersed in a 1:1 DMSO/Glutaraldehyde solution in 0.05M HEPES buffer for 24 hours at 25° C. Following treatment, the biological material is washed in sterile buffered saline and fabricated into bioprosthetic heart valves.

EXAMPLE 10

Fresh biological material is immersed in a 1:1 DMSO/Glutaraldehyde solution in 0.05M HEPES buffer for 24 hours, at a temperature of 25° C. Following immersion, the biological material is washed thoroughly in sterile buffered saline and further stabilized in glutaraldehyde, for example, 0.45% solution in 0.05M HEPES buffer. The glutaraldehyde-preserved biological material can then be fabricated into bioprosthetic heart valves and stored in glutaraldehyde at 4° C. for prolonged periods of time.

EXAMPLE 11

Freshly harvested biological material is stabilized in a 0.45% glutaraldehyde solution in 0.05M HEPES buffer before being immersed in DMSO for 1 hour at 25° C. Following treatment, the biological material is washed in sterile buffered saline and fabricated into bioprosthetic heart valves.

EXAMPLE 12

The procedure described in Example 11 is followed, except that an immersion temperature of 37° C. is used.

EXAMPLE 13

Freshly harvested biological material is stabilized in a 0.45% glutaraldehyde solution in 0.05M HEPES buffer before being immersed in a solution of 70% DMSO in 0.05M HEPES buffered water or saline for 1 hour at 25° C. Following treatment, the biological material is washed in sterile buffered saline and fabricated into bioprosthetic heart valves.

EXAMPLE 14

The procedure described in Example 13 is followed, except that an immersion temperature of 37° C. is used.

EXAMPLE 15

Freshly harvested biological material is stabilized with 0.45% glutaraldehyde solution in 0.05M HEPES buffer for 24 hours. The stabilized material is immersed for 1 hour in 70% DMSO/30% HEPES buffered saline at 25° C. Following treatment, the biological material is washed in sterile buffered saline and fabricated into bioprosthetic heart valves.

EXAMPLE 16

The procedure described in Example 15 is followed, except that an immersion temperature of 37° C. is used.

EXAMPLE 17

Porcine aortic root may be obtained from the abattoir and kept at 4° C. The tissue may be trimmed and processed with 0.45% buffered glutaraldehyde solution. The treated tissue may then be removed from the glutaraldehyde solution, rinsed, and placed in 100% buffered DMSO for 6 hours at room temperature. This tissue may then be removed from the DMSO solution and replaced in 0.45% buffered glutaraldehyde solution for 48 hours, removed, and fabricated into valves. The valves are then sterilized and prepared for implant.

IN VIVO EVALUATION-BIOLOGICAL TISSUE IN RAT SUBCUTANEOUS MODEL

Biological tissue samples in the form of porcine aortic cusps were removed from the aortic heart valves and immediately placed in buffered saline. The samples were then immersed in DMSO for 24 hours at ambient room temperature, rinsed copiously with sterile buffered saline and stabilized in 0.45% glutaraldehyde buffered with 0.05M HEPES.

A further group of samples of biological material was freshly harvested and fixed in 0.45% glutaraldehyde buffered with 0.05M HEPES before immersion in DMSO for 24 hours at ambient temperature.

A control group of samples were treated in 0.45% glutaraldehyde buffered with 0.05M HEPES only. All of the samples were rinsed in sterile buffered saline and implanted in subcutaneous pouches dissected in the ventral abdominal wall of weanling male rats (Sprague-Dawley, male, 3-week old, weighing 80–100 g). Each rat received 4 implants.

After 21 days, the rats were sacrificed by carbon dioxide asphyxiation and the tissue samples removed. These samples were analyzed for calcium using atomic absorption spectrometry. Additional samples were prepared for histological examination and scanning electron microscopy (SEM). The mechanical properties of the retrieved samples were analyzed by differential scanning calorimetry (DSC). Table 1 summarizes the calcium content of the samples (N refers to the number of samples).

TABLE 1

TISSUE CALCIUM LEVELS AFTER 21 DAY POST IMPLANT

| Treatment | N | Tissue $Ca^{2+}$ mg/g |
|---|---|---|
| DMSO-GA[1] | 22 | 3.08 |
| GA-DMSO[2] | 21 | 4.65 |
| CONTROL | 13 | 111.58 |

[1]Biological material immersed in DMSO followed by glutaraldehyde fixation
[2]Biological material fixed in glutaraldehyde followed by immersion in DMSO Comparison of the calcification levels for both methods of DMSO treatment (i.e. either before or after glutaraldehyde fixation) revealed no significant difference. This shows that the DMSO immersion step can be incorporated into fabrication of medical implant devices with minimal revision of standard manufacturing practices. Calcification of the biological materials was significantly inhibited both treatment methods using DMSO.

Similar results are set forth below in Table 2 for implant periods of 60, 90, and 120 days.

TABLE 2

TISSUE CALCIUM LEVELS AFTER VARIOUS IMPLANT PERIODS

| Implant Period | N | Tissue $Ca^{2+}$ mg/g |
|---|---|---|
| 60 days[1] | 15 | 3.95 |
| 60 days[2] | 15 | 3.65 |
| 60 days[3] | 11 | 208.37 |
| 90 days[1] | 13 | 8.44 |
| 90 days[2] | 13 | 5.50 |
| 90 days[3] | 9 | 224.45 |
| 120 days[1] | 8 | 68.00 |
| 120 days[2] | 12 | 3.37 |
| 120 days[3] | 5 | 217.69 |

[1]Biological material immersed in DMSO followed by glutaraldehyde fixation
[2]Biological material fixed in glutaraldehyde followed by immersion in DMSO
[3]Control (glutaraldehyde only)

The biological material treated according to the process of this invention can be surgically implanted in a manner known in the art to be useful for fixed or glutaraldehyde-treated biological material, in accordance with art-recognized procedures. The present invention may be used to prepare biological material suitable for use as replacement heart valves, skin patches, cardiac patches, pericardial patches, aortic patches, vascular grafts, replacement ligaments or tendons, tympanic membranes, or to prepare injectable collagen, by following methods known in the art.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An ex vivo method of treating a biological material to inhibit in vivo calcification of said biological material after implantation into a human or animal body, wherein said method includes a dimethyl sulfoxide contacting step:

the dimethyl sulfoxide contacting step consists essentially of:

contacting said biological material ex vivo with neat dimethyl sulfoxide in an amount and for a period of time sufficient to inhibit calcification of said biological material after implantation into a human or animal body, thereby treating said biological material; and preserving said biological material by contacting the biological material with glutaraldehyde ex vivo;

wherein said biological material is a natural or synthetic material suitable for implantation in vivo, and wherein said dimethyl sulfoxide contacting step is performed after thawing when said biological material is cryopreserved.

2. The method according to claim 1, wherein said preserving is carried out prior to said contacting with said dimethyl sulfoxide.

3. The method according to claim 1, wherein said preserving is carried out subsequent to said contacting with said dimethyl sulfoxide.

4. The method according to claim 1, wherein said contacting comprises immersing said biological material in said dimethyl sulfoxide at a temperature of from about 18° C. to about 60° C.

5. The method according to claim 4, wherein said immersing is conducted for a time period ranging from about three minutes to about 48 hours.

6. The method of claim 1, wherein said biological material is a natural biological tissue of animal origin.

7. The method according to claim 6, wherein said biological tissue is selected from the group consisting of heart valves and pericardium.

8. The method according to claim 7, wherein said heart valves and pericardium are obtained from cattle, pigs, horses, yak, or kangaroo.

9. The method according to claim 1, wherein said biological material is a human homograft.

10. The method according to claim 1, wherein said biological material is synthetically derived.

11. The method according to claim 10, wherein said biological material is reconstituted collagen.

12. A dimethyl sulfoxide treated biological material prepared according to the method recited in claim 1.

* * * * *